(12) United States Patent
Kaizik et al.

(10) Patent No.: US 6,627,782 B2
(45) Date of Patent: Sep. 30, 2003

(54) PREPARATION OF 1-OLEFINS

(75) Inventors: Alfred Kaizik, Marl (DE); Wilfried Bueschken, Haltern (DE); Klaus-Diether Wiese, Haltern (DE); Guido Protzmann, Zwingenberg (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 10/067,924

(22) Filed: Feb. 8, 2002

(65) Prior Publication Data

US 2002/0169347 A1 Nov. 14, 2002

(30) Foreign Application Priority Data

Feb. 10, 2001 (DE) .......................................... 10106185
Sep. 27, 2001 (DE) .......................................... 10147775

(51) Int. Cl.⁷ ............................. C07C 1/00; C07C 29/14
(52) U.S. Cl. ...................... 585/639; 585/640; 568/880; 568/881
(58) Field of Search ................................ 585/640, 639; 568/880, 881

(56) References Cited

U.S. PATENT DOCUMENTS

| 5,093,534 A | * | 3/1992 | Ludwig et al. |
| 5,130,287 A | | 7/1992 | Sweeney |
| 5,210,363 A | | 5/1993 | Sweeney |
| 6,340,778 B1 | * | 1/2002 | Bueschken et al. |

FOREIGN PATENT DOCUMENTS

| EP | 0 326 674 | 8/1989 |
| EP | 0 470 344 | 2/1992 |
| GB | 1 225 559 | 3/1971 |
| GB | 1 233 020 | 5/1971 |

OTHER PUBLICATIONS

Solomons Organic Chemistry, 1992, John Wiley & Sons, New York, pp. 739–740.*

* cited by examiner

*Primary Examiner*—Johann Richter
*Assistant Examiner*—Paul A. Zucker
(74) *Attorney, Agent, or Firm*—Oblon, Spivak, McClelland, Maier & Neustadt, P.C.

(57) ABSTRACT

A multi-stage synthesis is effective for preparing 1-olefins from aldehydes. The aldehyde is condensed with acetone to form an α,β-unsaturated ketone. The unsaturated ketone is hydrogenated to yield a saturated alcohol. By dehydrating the saturated alcohol a 1-olefin is obtained. The olefin can be isolated in high yield and purified.

14 Claims, 1 Drawing Sheet

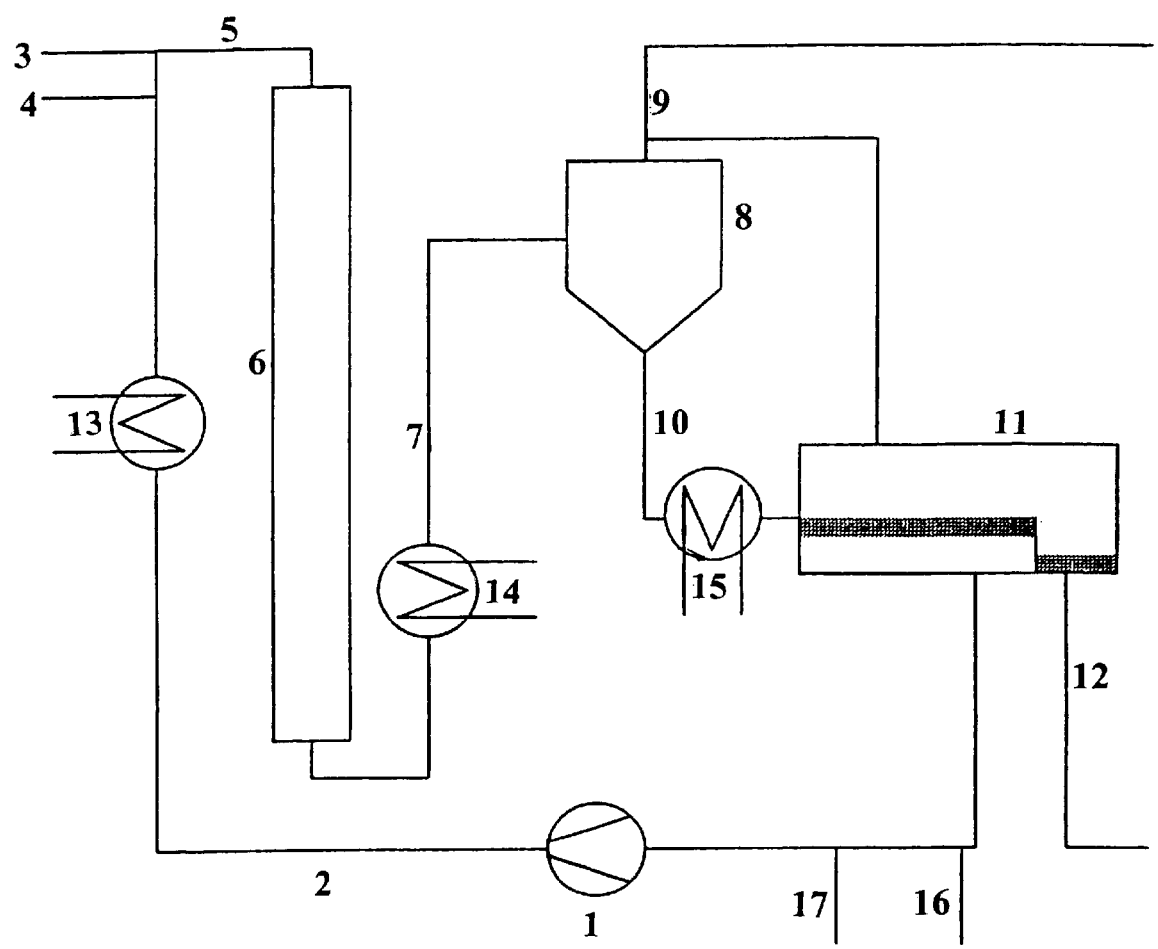

PREPARATION OF 1-OLEFINS

BACKGROUND OF THE INVENTION

1. Field of the Invention

The invention relates to the preparation of 1-olefins from aldehydes by means of a three-stage synthesis.

2. Discussion of the Background

Owing to their reactivity, olefins are among the most important synthetic building blocks in organic chemistry. They are precursors for many compounds, for example aldehydes, ketones, alcohols, carboxylic acids and halogen compounds. They are used in large quantities for the preparation of homo-oligomers or co-oligomers and homopolymers and copolymers, for example polyethylene or polypropylene.

Ethylene and propylene are prepared in large quantities throughout the world by steam cracking or by catalytic cracking of hydrocarbons. These processes also produce considerable amounts of $C_4$-olefins (isobutene, 1-butene, 2-butenes) and to a lesser extent $C_{5+}$-olefins. Higher 1-olefins are mostly produced by chain buildup reactions.

Ethylene can be oligomerized with the aid of Ziegler catalysts to give a mixture of unbranched 1-olefins having an even number of carbon atoms.

In a variant of the SHOP process, unbranched 1-olefins having an even or odd number of carbon atoms can be prepared from ethylene. This process comprises three reaction steps, namely ethylene oligomerization, isomerization, i.e., a shift of the double bonds, and cross-metathesis of the olefin mixture having internal double bonds with ethylene.

Dehydrogenation of straight-chain paraffins, for example by chlorination and dehydrochlorination, forms olefins having predominantly internal double bonds which can be converted by cross-metathesis into 1-olefins. The above-mentioned processes all have the disadvantage that a large number of 1-olefins is always produced.

Straight chain 1-olefins having an even number of carbon atoms can be obtained from fatty alcohols by elimination of water. Disadvantages of this method are the high price of the starting materials and the fact that essentially only fatty alcohols having from 12 to 18 carbon atoms are available in sufficient quantities.

Since the known methods do not give all desired 1-olefins in a sufficiently large quantity and/or in a sufficiently high purity, there is a need for a method of preparing 1-olefins from readily available starting materials.

It has now been found that 1-olefins can be prepared from aldehydes by aldol condensation with acetone, hydrogenation of the α,β-unsaturated ketones to form the unsaturated alcohols and subsequent elimination of water from alcohols.

SUMMARY OF THE INVENTION

The invention accordingly provides a process for preparing 1-olefins having from 7 to 24 carbon atoms from aldehydes having from 4 to 21 carbon atoms, which comprises condensing an aldehyde with acetone to form an α,β-unsaturated ketone, hydrogenating the unsaturated ketone obtained in this way to form the saturated alcohol and eliminating water from the saturated alcohol.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein: a schematic diagram of the reaction apparatus is presented.

DESCRIPTION OF THE PREFERRED EMBODIMENTS

Referring now to the drawings, wherein like reference numerals designate identical or corresponding parts throughout the several views.

In the process of this invention, it is possible to use aldehydes or aldehyde mixtures having from 4 to 21 carbon atoms. The aldehydes used can originate from various sources. It is possible to use aldehydes which have been obtained by dehydrogenation of alcohols, for example, fatty alcohols. Likewise, aldehydes from cleavage reactions, for example heptanal from methyl ricinoleate, can be used as starting materials. In particular, it is possible to use aldehydes which have been produced by hydroformylation of olefins.

Furthermore, unsaturated aldehydes formed by self-condensation of an aldehyde, e.g., 2-ethylhex-2-enal from n-butyraldehyde, can also be used.

For example, the aldehydes mentioned below can serve as starting material for the process of the invention:

n-butyraldehyde, isobutyraldehyde, crotonaldehyde, valeraldehyde, 2-methylbutanal, 3-methylbutanal, dimethylpropanol, tiglinaldehyde, 3,3-dimethylacrolein, n-hexanal, isohexanal, n-heptanal, citral, α- and β-citral, benzaldehyde, cinnamaldehyde, phenylacetaldehyde, hydrocinnamaldehyde, 2-phenylpropionaldehyde, cyclohexyl carbaldehyde, anisaldehyde; aldehyde mixtures prepared by hydroformylation of dipropene, dibutene, tripropene, tetrapropene, tributene, pentapropene, tetrabutene.

A preferred starting material is n-pentanal.

The aldol condensation of aldehydes with acetone to form α,β-unsaturated ketones is preferably carried out as a two-phase reaction. The reaction is, as described in DE 199 57 522, the disclosure of which is hereby expressly incorporated by reference, carried out in a tube reactor, with the catalyst being present in the continuous phase and the starting material being present in a disperse phase and the loading factor B of the reactor being equal to or greater than 0.8 and the mass ratio of the catalyst phase to organic phase being greater than 2. (The loading factor B is defined as follows: B=PD/PS. PD [Pa/m] is a pressure dropper unit length over the reactor under operating conditions and PS [Pa/m] is a mathematical parameter having the dimensions of pressure per unit length, defined as the ratio of mass flow M [kg/s] of all components under operating conditions multiplied by $g=9/81$ [m/s$^2$], i.e., PS=(M/V)*g.)

As catalyst phases, preference is given to using aqueous solutions of hydroxides, hydrogen carbonates, carbonates and carboxylates in the form of their alkali metal or alkaline earth metal compounds, in particular sodium hydroxide and potassium hydroxide. The concentration of the catalyst in the catalyst solution is from 0.1 to 15% by mass, in particular from 0.1 to 5% by mass.

Aldehyde, acetone and optionally a solvent are introduced into the catalyst phase upstream of the reactor. The molar ratio of aldehyde to acetone is from 5/1 to 1/10, preferably from 1/1 to 1/5. The reaction is carried out in a temperature range from 40° C. to 150° C., preferably in the range from 50° C. to 120° C. The reaction time is from 0.1 to 20 minutes, preferably from 0.2 to 10 minutes.

The catalyst phase is separated off from the product mixture leaving the reactor and is recirculated to the reactor. Before the phase separation, unreacted starting materials, some product, water and optionally solvent are preferably distilled off. After condensation, the distillate separates into an aqueous phase and an organic phase which is returned to the reactor. Starting materials, in particular acetone, are distilled off from the aqueous phase and part of the aqueous phase is then discarded to discharge the water of reaction from the system and part of it is, after optional use as scrubbing liquid, returned to the process. The product phase which has been separated off from the catalyst can, if desired after scrubbing with water, be worked up by distillation to give the pure α,β-unsaturated ketone. Another possibility is to use the crude product in the next stage. This procedure enables the desired α,β-unsaturated ketone to be prepared highly selectively.

Any organic solvent added to the starting material or to the product mixture from the reaction has to have the following properties: it dissolves products and starting materials and is itself sparingly soluble in the catalyst phase. It is inert toward the aldol condensation and optionally in the hydrogenation. It can be separated by distillation from the intermediate, namely the α,β-unsaturated ketone and/or the subsequent product, namely the saturated alcohol. Preferred solvents are those which form a minimum heteroazeotrope with water, so that water can easily be separated from the α,β-unsaturated ketone by distillation. Examples of suitable solvents are ethers, hydrocarbons such as cyclohexane or toluene.

The unsaturated ketone obtained as intermediate can not only be converted into a 1-olefin as claimed in the process of the present invention but can also be utilized for other syntheses. Thus, hydrogenation of the unsaturated ketone can give a saturated ketone. This product could be an intermediate for a saturated alcohol or an olefin having an internal double bond.

The α,β-unsaturated ketone obtained by crossed aldol condensation according to the process of the invention is hydrogenated in pure form or as a mixture which can further comprise acetone, starting aldehyde, water, solvent and high boilers to give the corresponding saturated alcohols.

The hydrogenation is preferably carried out in the liquid phase.

The hydrogenation can be carried out using catalysts or catalyst systems which hydrogenate both olefinic double bonds and carbonyl groups. Particularly useful catalysts for the hydrogenation of the α,β-unsaturated ketones are, in particular, those which are used for the hydrogenation of 2-ethylhex-2-enal to 2-ethylhexanol.

The hydrogenation can be carried out using, for example, copper/nickel, copper/chromium, copper/chromium/nickel, zinc/chromium, nickel/molybdenum catalyst. It is also possible to use combinations of two or more catalysts. The catalysts can be unsupported or the hydrogenation-active substances or their precursors can have been applied to supports such as silicon dioxide or aluminum oxide.

Preferred catalysts over which the α,β-unsaturated ketones are hydrogenated comprise 0.3–15% by mass of copper, 0.3–15% by mass of nickel and, as activators, 0.05–3.5% by mass of chromium and advantageously 0.01–1.6% by mass, preferably 0.02–1.2% by mass, of an alkali metal component on a support material, preferably aluminum oxide or silicon dioxide. The amounts stated are based on the catalyst before it is reduced. The alkali metal component is optional.

The catalysts are advantageously used in a form in which they offer a low resistance to flow, e.g., in the form of granules, pellets, or shaped bodies such as tablets, cylinders, rod extrudates or rings. They are advantageously activated, e.g., by heating in a stream of hydrogen, before use.

The hydrogenation, preferably a liquid-phase hydrogenation, is generally carried out under a total pressure of from 5 to 200 bar, in particular from 5 to 30 bar, very particularly preferably from 15 to 25 bar. A hydrogenation in the gas phase can also be carried out at lower pressures with correspondingly large gas volumes. If a plurality of hydrogenation reactors are employed, the total pressures in the individual reactors can be identical or different within the above-mentioned pressure limits.

The reaction temperatures in the hydrogenation in the liquid or gaseous phases are generally in the range from 120 to 220° C., in particular from 140 to 180° C.

Examples of such hydrogenations are described in patent applications EP 0 470 344 A2 and EP 0 326 674 A2.

The hydrogenation of 3-octen-2-one to octan-2-ol can optionally be carried out in two stages. In this case, the olefinic double bond is hydrogenated over, for example, a palladium catalyst in the first stage and the carbonyl group is hydrogenated over one of the above-mentioned catalysts in the second stage.

The saturated alcohols obtained in the second reaction step are used in the third step of the process of the invention. Furthermore, they can also be used as solvents or for producing plasticizers or detergents.

The elimination of water from 2-alcohols generally gives a mixture of 1- and 2-olefins. The catalytic dehydration of 2-alcohols to form predominantly 1-olefins is known from the literature. Thus, for example, gas-phase processes in which the elimination of water is carried out in the temperature range from 250 to 350° C. over aluminum oxide or zirconium oxides are disclosed in U.S. Pat. Nos. 5,130,287, 5,210,363, GB 1225559 and GB 1233020.

Accordingly, the preparation of the 1-olefins is carried out in the process of the invention by dehydration of 2-alcohols in the gas phase or a gas/liquid mixed phase over a fixed-bed catalyst.

The reaction mixture can, if desired after removal of water, be separated by distillation into starting alcohol, olefins and by-products. The unreacted alcohol can be returned to the dehydration step.

If the olefin fraction further comprises olefins other than the target product, the pure 1-olefin can be isolated from it by distillation.

The 1-olefins obtained by the process of the invention can be used as monomers or comonomers in the preparation of oligomers or polymers. They can serve as starting compounds for the preparation of epoxides, ketones, aldehydes, alcohols and carboxylic acids. Furthermore, they can be used as alkylating agents or as components in diene reactions. Monobranched olefins, in particular those having a methyl branch on the second or penultimate carbon atom, are suitable for preparing tertiary carboxylic acids by the Koch synthesis. Here, the important fact is not the position of the double bond but the type of branching which is determined, inter alia, by the process of the invention.

The advantage of the process of the invention is that 1-olefins can be prepared from readily available aldehydes, with the degree of branching of the olefin prepared corresponding to that of the starting aldehyde. Thus, for example, 1-octene can be prepared from n-pentanal which can be obtained by hydroformylation of linear butenes.

The following examples illustrate the invention without restricting its scope.

EXAMPLE 1

Condensation of Acetone and Pentanal to Form 3-octen-2-one

The first table accompanying example 1 shows firstly the catalyst composition and then the amount of feed and its composition. The product composition is listed in the lower part of the second table. The upper part of the second table reports the space-time yield (STY), the conversion (C) of the aldehyde, the selectivity (S) to the desired aldol condensation products and the loading factor (B). In the case of the catalyst composition described, it should be noted that the values given in the examples are initial values. The proportion of NaOH was slightly diluted by water of reaction formed in the aldol condensation. Furthermore, the Cannizzaro reaction which proceeds in parallel to the aldol condensation leads to neutralization of the alkaline catalyst. However, both effects are so small over the time in question that they are inconsequential for the description of the experiment and the experimental result.

The aldolization was carried out in a test apparatus which is shown schematically in the drawing. Here, the continuous catalyst phase 2 is circulated by means of a pump 1. The aldehyde or the aldehyde mixture is mixed into the catalyst via line 3 or different aldehydes are mixed in separately via lines 3 and 4. In the example described below, the starting materials were mixed in exclusively via line 3. The multiphase mixture 5 is pumped through the tube reactor 6 which has a length of 3 m and a diameter of 17.3 mm and was provided with static mixing elements having a hydraulic diameter of 2 mm. The resulting mixture 7, comprising the reaction product, unreacted starting material and the catalyst, can be freed of volatile constituents in the gas separator 8 by discharge of the latter into line 9. In the example described below, this line was closed.

The liquid stream 10 obtained after the degassing step 8 is passed to a phase separation vessel 11. Hence, the aqueous catalyst phase 2 is separated off and returned to the circuit. The organic phase which has flowed over a weir and contains the reaction product is taken off via line 12.

The heat of reaction can be removed by heat exchangers 13, 14 and 15 located outside the reactor.

The example describes aldol condensation of acetone (Ac) and pentanal (PAL) to form 3-octene-2-one (3-ON). The formation of the by-products 4-methyl-3-penten-2-one (4-MP), 4-hydroxy-4-methyl-3-pentan-2-one (4-HMP), 4-hydroxy-3-octan-2-one (4-HON), 2-propyl-2-heptenal (2-PHL) and the other high boilers (HB) are reported in % by mass in the table below.

The reaction mixture was passed through the reactor at a catalyst throughput of 400 kg/h at a temperature 80° C. under the autogenous pressure of the reaction participants.

TABLE 1

| | |
|---|---|
| Catalyst [g] | 4981 |
| c NaOH [% by mass] | 4.0 |
| Water [% by mass] | 91.8 |
| Acetone [% by mass] | 4.2 |
| Feed [1/h] | 4.28 |
| Ac [% by mass] | 48.04 |
| PAL [% by mass] | 51.96 |

The following result was achieved:

TABLE 2

| | |
|---|---|
| STY [t/m³/h] | 2.1 |
| C [%] | 0.95 |
| S [%] | 64.0% |
| B | 14.72 |
| Ac [% by mass] | 22.52 |
| PAL [% by mass] | 3.04 |

TABLE 2-continued

| | |
|---|---|
| 4-MP [% by mass] | 0.35 |
| 4-HMP [% by mass] | 0.23 |
| 3-ON [% by mass] | 47.46 |
| 4-HON [% by mass] | 8.03 |
| 2-PHL [% by mass] | 9.49 |
| HB [% by mass] | 8.88 |

In Table 2, the selectivity relates to the formation of 3-octen-2-one; based on the sum of 3-octen-2-one and 4-hydroxy-3-octan-2-one, the selectivity is 74%.

EXAMPLE 2

Hydrogenation of 3-octen-2-one to Form 2-octanol

One liter of a mixture obtained from the crude reaction product of example 1 by distilling off the low boilers, acetone and pentanal was hydrogenated in the liquid phase in a circulation apparatus for 3 hours at 160° C. and 25 bar absolute over 100 g of a Cu/Cr/Ni catalyst on an $Al_2O_3$ support. The analysis of the feed and the composition of the hydrogenation product after running the experiment for 3 hours are shown in Table 3.

TABLE 3

| Component | Feed for the Hydrogenation (% by mass) | Product of the hydrogenation (% by mass) |
|---|---|---|
| Acetone | 0.01 | 0.01 |
| Pentanal | 0.25 | 0.00 |
| Isopropanol | 0.00 | 0.95 |
| 1-Pentanol | 0.00 | 1.73 |
| 3-Octen-2-one | 63.65 | 0.00 |
| 2-Octanol | 0.00 | 73.25 |
| 4-hydroxy-3-octan-2-one | 10.79 | 0.00 |
| 3-Octan-2-one | 0.00 | 1.05 |
| 4-Methyl-3-penten-2-one | 0.48 | 0.00 |
| 4-Hydroxy-4-methyl-3-penten-2-one | 0.35 | 0.05 |
| 4-Methyl-2-pentanol | 0.00 | 0.72 |
| 2-Propyl-2-heptanal | 12.72 | 0.00 |
| 2-Propylheptanol | 0.00 | 12.15 |
| High boilers | 11.75 | 10.09 |

As can be seen from Table 3, 3-octen-2-one and 4-hydroxy-3-octen-2-one are hydrogenated with high selectivity (>97%) to the desired product 2-octanol.

EXAMPLE 3

Dehydration of 2-octanol to Give 1-octene

The output from the hydrogenation in Example 2 was freed of low boilers (pentanol isopropanol) and high boilers by distillation in a laboratory distillation apparatus and then used as starting material comprising about 98% by weight of 2-octanol and about 2% by weight of high boilers for the dehydration in the presence of an NaOH-modified zirconium oxide ($ZrO_2$ containing 1% by weight of $Na_2O$) in a flow-through fixed-bed reactor. Before entering the reactor, the liquid feed was vaporized at 220° C. in an upstream vaporizer. At a reaction temperature of 325° C. in the rector, 20.1 g/h (=24.5 ml/h) of feed were passed as gas through 35.7 g (~30 ml) of catalyst in pellet form, corresponding to an LHSV of 0.82 $h^{-1}$. The gaseous product was cooled in a condenser and collected in liquid form in a glass receiver.

The GC analysis of the dehydration product is shown in Table 4.

TABLE 4

Dehydration of 2-octanol over a $ZrO_2$ catalyst

| Component | Products of the cracking of 2-octanol (% by weight) |
|---|---|
| 1-Octene | 57.60 |
| tr-4-Octene | 0.00 |
| tr-3-Octene/cis-4-octene | 0.01 |
| cis-3-Octene | 0.02 |
| tr-2-Octene | 1.73 |
| cis-2-Octene | 0.99 |
| 2-Octanone | 7.10 |
| 2-Octanol | 29.55 |
| Dioctylether | 0.25 |
| High boilers | 0.25 |

As can be seen from Table 4, the 2-octanol is dehydrated with high selectivity (>95%) to the desired product 1-octene. After the desired product and the by-products have been separated off by distillation, the unreacted 2-octanol can be returned to the dehydration reactor. The 2-octanone formed as by-product can be hydrogenated to 2-octanol.

Obviously, numerous modifications and variations of the present invention are possible in light of the above teachings. It is therefore to be understood that within the scope of the appended claims, the invention may be practiced otherwise than as specifically described herein.

German applications DE 101 06 185.4 and DE 101 47775.9, filed on Feb. 10, 2001 and Sep. 27, 2001 respectively, are incorporated herein by reference.

What is claimed is:

1. A process for preparing one or more 1-olefins which comprises
    condensing an aldehyde with acetone in a tube reactor having a loading factor of greater than 0.8, thereby forming an $\alpha,\beta$-unsaturated ketone,
    hydrogenating said $\alpha,\beta$-unsaturated ketone to form a saturated alcohol, and
    eliminating water from said saturated alcohol to form said one or more 1-olefins,
    wherein said aldehyde has from 4 to 21 carbon atoms and said one or more 1-olefins has from 7 to 24 carbon atoms.

2. The process as claimed in claim 1, wherein the hydrogenation is carried out in the liquid phase.

3. The process as claimed in claim 1, wherein the $\alpha,\beta$-unsaturated ketone is hydrogenated over a fixed-bed catalyst, said fixed-bed catalyst comprising copper, chromium, and nickel, to form the saturated alcohol.

4. The process as claimed in claim 1, wherein the elimination of water from the saturated alcohol is carried out in the gas phase or in a gas/liquid mixed phase over a fixed-bed catalyst.

5. The process as claimed in claim 1, wherein the 1-olefin is 1-octene and the aldehyde is n-pentanal.

6. The process as claimed in claim 1, wherein the condensation takes place in the presence of a catalyst.

7. The process as claimed in claim 6, wherein said catalyst is sodium hydroxide or potassium hydroxide.

8. The process as claimed in claim 1, wherein a molar ratio of the aldehyde to the acetone is from 1/1 to 1/5.

9. The process as claimed in claim 1, wherein said condensing is carried out at a temperature of from 50° C. to 120° C.

10. The process as claimed in claim 1, wherein said condensation and/or said hydrogenation is carried out in an organic solvent.

11. The process as claimed in claim 10, wherein the organic solvent is an ether or a hydrocarbon.

12. The process as claimed in claim 11, wherein the hydrocarbon is cyclohexane or toluene.

13. The process as claimed in claim 3, wherein the fixed bed catalyst comprises from 0.3 to 15% copper, from 0.3 to 15% nickel and from 0.05 to 3.5% chromium by mass.

14. The process as claimed in claim 1, wherein said hydrogenation is carried out at a pressure of from 15 to 25 bar.

* * * * *